United States Patent
Kim et al.

(10) Patent No.: US 10,294,111 B2
(45) Date of Patent: May 21, 2019

(54) METHOD OF PREPARING HYDROPHOBIC SILICA AEROGEL AND HYDROPHOBIC SILICA AEROGEL PREPARED THEREBY

(71) Applicant: LG CHEM, LTD., Seoul (KR)

(72) Inventors: Young Hun Kim, Daejeon (KR); Jin Hee Oh, Daejeon (KR); Je Kyun Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 19 days.

(21) Appl. No.: 15/527,663

(22) PCT Filed: Nov. 4, 2016

(86) PCT No.: PCT/KR2016/012671
§ 371 (c)(1),
(2) Date: May 17, 2017

(87) PCT Pub. No.: WO2017/090912
PCT Pub. Date: Jun. 1, 2017

(65) Prior Publication Data
US 2017/0369326 A1 Dec. 28, 2017

(30) Foreign Application Priority Data

Nov. 27, 2015 (KR) .......................... 10-2015-0167861

(51) Int. Cl.
*C01B 33/154* (2006.01)
*C01B 33/159* (2006.01)
*C01B 33/158* (2006.01)
*C07F 7/10* (2006.01)
*C09C 1/30* (2006.01)

(52) U.S. Cl.
CPC .......... *C01B 33/154* (2013.01); *C01B 33/159* (2013.01); *C01B 33/1585* (2013.01); *C07F 7/10* (2013.01); *C09C 1/30* (2013.01); *C09C 1/3018* (2013.01); *C09C 1/3027* (2013.01); *C09C 1/3081* (2013.01); *C01P 2006/11* (2013.01)

(58) Field of Classification Search
None
See application file for complete search history.

(56) References Cited

U.S. PATENT DOCUMENTS

| | | | |
|---|---|---|---|
| 5,811,031 A | 9/1998 | Jansen et al. | |
| 7,470,725 B2 * | 12/2008 | Schwertfeger | B01J 13/0091 106/490 |
| 8,894,893 B2 * | 11/2014 | Ahn | C01B 33/1585 264/13 |
| 2001/0034375 A1 | 10/2001 | Schwertfeger et al. | |
| 2012/0128958 A1 * | 5/2012 | Zeng | C01B 33/1585 428/219 |

FOREIGN PATENT DOCUMENTS

| | | |
|---|---|---|
| CN | 1241952 | 1/2000 |
| EP | 0658513 | 6/1995 |
| KR | 100566390 B1 | 3/2006 |
| KR | 20080084241 A | 9/2008 |
| KR | 20090115703 A | 11/2009 |
| KR | 20120126741 A | 11/2012 |
| KR | 20150093062 A | 8/2015 |
| WO | 199823366 | 6/1998 |

OTHER PUBLICATIONS

Moshtaghioun et al., Int. Journal of Refractory Metals and Hard Materials 29 (2011) 645-650. (Year: 2011).*
Discussion Material for Examiner Interview; Jan. 11, 2019 (Year: 2019).*
Shewale et al., "Synthesis and characterization of low density and hydrophobic silica aerogels dried at ambient pressure using sodium silicate precursor," J Porous Mater 16: 101-108 (2009).

* cited by examiner

*Primary Examiner* — Clinton A Brooks
*Assistant Examiner* — Kofi Adzamli
(74) *Attorney, Agent, or Firm* — Dentons US LLP

(57) ABSTRACT

The present invention relates to a method of preparing a high hydrophobic silica aerogel having a low tap density and a hydrophobic silica aerogel prepared thereby. The method of preparing a hydrophobic silica aerogel according to the present invention may have good productivity and economic efficiency, because preparation time is reduced by simultaneously performing surface modification and solvent substitution in a single step, and may control a degree of hydrophobicity of the prepared silica aerogel by controlling a surface modification reaction by including a step of adding ammonium hydroxide. Thus, a hydrophobic silica aerogel having excellent physical properties, such as tap density and specific surface area, as well as high hydrophobicity obtained by controlling the degree of hydrophobicity may be prepared.

13 Claims, 1 Drawing Sheet

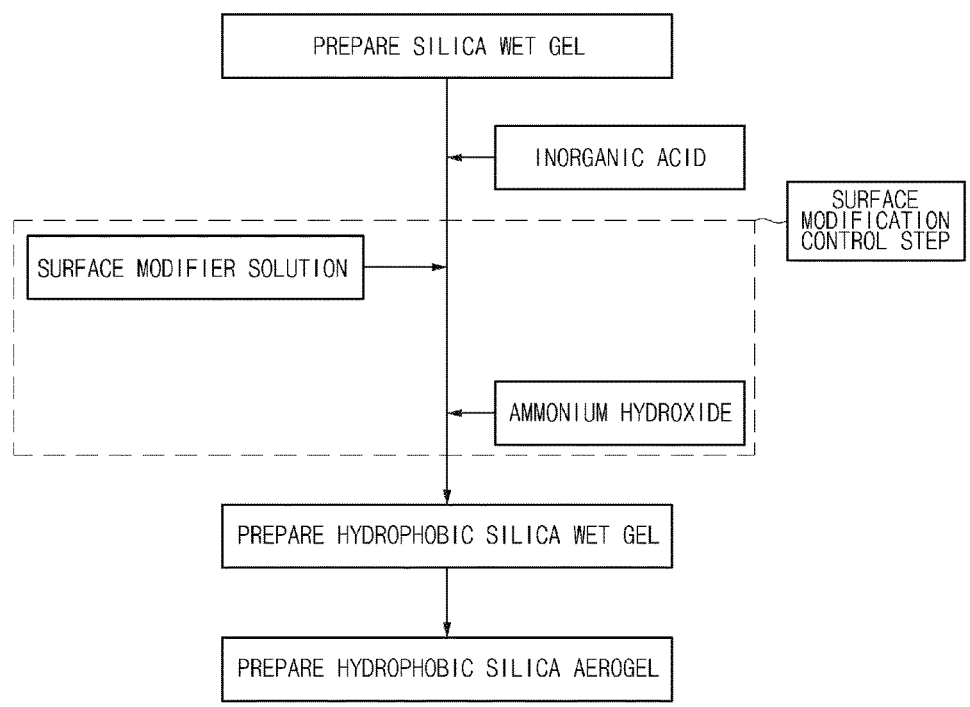

METHOD OF PREPARING HYDROPHOBIC SILICA AEROGEL AND HYDROPHOBIC SILICA AEROGEL PREPARED THEREBY

This application is a National Stage Application of International Application No. PCT/KR2016/012671, filed Nov. 4, 2016, and claims the benefit of Korean Patent Application No. 10-2015-0167861, filed Nov. 27, 2015, the contents of which are incorporated herein by reference in their entirety for all purposes as if fully set forth below.

CROSS-REFERENCE TO RELATED APPLICATIONS

This application claims the benefit of Korean Patent Application No. 10-2015-0167861, filed on Nov. 27, 2015, in the Korean Intellectual Property Office, the disclosure of which is incorporated herein in its entirety by reference.

TECHNICAL FIELD

The present invention relates to a method of preparing a high hydrophobic silica aerogel having a low tap density and a hydrophobic silica aerogel prepared thereby.

BACKGROUND ART

Since an aerogel, as a high specific area ($\geq 500$ m$^2$/g), ultra-porous material having a porosity of about 90% to about 99.9% and a pore diameter of about 1 nm to about 100 nm, has excellent characteristics such as ultra lightweightness, ultra insulation, and ultra-low dielectric constant, research into the applications of the aerogel as a transparent insulator and an environmentally-friendly high-temperature insulator, an ultra-low dielectric thin film for a highly integrated device, a catalyst and a catalyst support, an electrode for a supercapacitor, and an electrode material for desalination as well as the development of an aerogel material has been actively conducted.

The biggest advantage of the aerogel is super-insulation having a thermal conductivity of 0.300 W/m·K or less which is lower than that of an organic insulation material such as a typical Styrofoam. Also, the aerogel may address fire vulnerability and generation of toxic gas in case of fire, i.e., fatal weaknesses of a typical organic insulation material.

In general, a wet gel is prepared from a silica precursor such as water glass or tetraethoxysilane (TEOS), and an aerogel is then prepared by removing a liquid component in the wet gel without destroying its microstructure. A silica aerogel may be categorized into three typical forms, powder, granules, and monolith, and the silica aerogel is generally prepared in the form of powder.

The silica aerogel powder may be commercialized in a form, such as an aerogel blanket or aerogel sheet, by compositing with fibers, and, since the blanket or sheet has flexibility, it may be bent, folded, or cut to a predetermined size or shape. Thus, the silica aerogel may be used in household goods, such as jackets or shoes, as well as industrial applications such as an insulation panel of a liquefied natural gas (LNG) carrier, an industrial insulation material and a space suit, transportation and vehicles, and an insulation material for power generation. Furthermore, in a case where a silica aerogel is used in a fire door as well as a roof or floor in a home such as an apartment, it has a significant effect in preventing fire.

However, since the silica aerogel powder may be scattered due to high porosity, very low tap density, and small particle size, handling may be difficult and fill may not be easy.

Also, although the silica aerogel monolith has high transparency in visible light region, the silica aerogel monolith may have a size limitation, may be difficult to be molded in various shapes, and may be easily broken.

In order to address the above-described limitations of the silica aerogel powder and monolith, attempts have been made to increase ease of handling and shape-responsiveness by preparing silica aerogel granules having a diameter of 0.5 mm or more. For example, there are methods such as the method in which a reaction solution obtained by hydrolyzing alkoxysilane is prepared as a filler, gelation is performed by polycondensation of the filler with a catalyst, a hydrophobic treatment is performed by reacting with a hydrophobic agent, and supercritical drying is then performed to obtain hydrophobic silica aerogel granules; and the method in which aerogel particles including additives and binder are supplied to a molding machine and compressed to prepare silica aerogel granules.

However, since the above-described methods use an ancillary granulating device and an additive such as a binder, technically complex process and long process time may not only be required, but complex processing procedures and high investment costs may also be required when a silica aerogel is mass-produced by the above-described methods. As a result, a lot of time and expensive chemicals are required, and accordingly, production costs may not only be increased, but also a particle size of the finally obtainable silica aerogel may not be uniform or may be excessively large.

Furthermore, since gel structure characteristics and physical properties are reduced when the silica aerogel absorbs moisture, there is a need to develop a method, which may permanently prevent the absorption of moisture in the air, for ease of use in industry. Thus, methods of preparing a silica aerogel having permanent hydrophobicity by performing a hydrophobic treatment on a surface of the silica aerogel have been proposed. In general, a silica aerogel having hydrophobicity is being prepared by using a surface modifier. However, in a case in which the surface of the silica aerogel is hydrophobized only with the surface modifier, since a large amount of the expensive surface modifier may be used and it may be difficult to control a surface modification reaction, productivity and economic efficiency are low and there are limitations in preparing a silica aerogel having high hydrophobicity.

Therefore, there is a need to develop a method which may prepare a silica aerogel having high hydrophobicity by controlling hydrophobicity while easily controlling a surface modification reaction.

DISCLOSURE OF THE INVENTION

Technical Problem

An aspect of the present invention provides a method of preparing a hydrophobic silica aerogel which may prepare a silica aerogel having high hydrophobicity by using a simple preparation process and easily controlling a surface modification reaction.

Another aspect of the present invention provides a hydrophobic silica aerogel prepared by the above preparation method.

Technical Solution

According to an aspect of the present invention, there is provided a method of preparing a hydrophobic silica aerogel including the steps of: adding an acid catalyst to a water glass solution and performing a reaction to prepare a silica wet gel (step 1); adding the silica wet gel to a reactor, adding an inorganic acid and a surface modifier solution thereto, and performing a reaction to prepare a hydrophobic silica wet gel (step 2); and drying the hydrophobic silica wet gel (step 3), wherein the method further includes adding ammonium hydroxide during the reaction of step 2.

According to another aspect of the present invention, there is provided a hydrophobic silica aerogel prepared by the above method.

Advantageous Effects

A method of preparing a hydrophobic silica aerogel according to the present invention may have good productivity and economic efficiency, because preparation time is reduced by simultaneously performing surface modification and solvent substitution in a single step, and may control a degree of hydrophobicity of the prepared silica aerogel by controlling a surface modification reaction by including a step of adding ammonium hydroxide.

Also, since a hydrophobic silica aerogel according to the present invention is prepared by the above preparation method, physical properties, such as tap density and specific surface area, may not only be excellent, but high hydrophobicity may also be obtained by controlling the degree of hydrophobicity.

Thus, the preparation method according to the present invention and the hydrophobic silica aerogel are suitable for industries that need the method and the hydrophobic silica aerogel, particularly, industries that need a silica aerogel having high hydrophobicity or industries that need a silica aerogel having various degrees of hydrophobicity.

BRIEF DESCRIPTION OF THE DRAWINGS

The following drawings attached to the specification illustrate preferred examples of the present invention by example, and serve to enable technical concepts of the present invention to be further understood together with detailed description of the invention given below, and therefore the present invention should not be interpreted only with matters in such drawings.

FIG. 1 schematically illustrates a flowchart of a method of preparing a hydrophobic silica aerogel according to an embodiment of the present invention.

MODE FOR CARRYING OUT THE INVENTION

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

The present invention provides a method of preparing a hydrophobic silica aerogel having improved surface hydrophobicity.

In general, a hollow of a silica wet gel prepared using water glass is filled with water, i.e., a solvent, and, when the solvent is simply removed by drying, shrinkage and cracking of a pore structure may easily occur due to high surface tension of water at a gas/liquid interface while the liquid phase solvent is evaporated into a gas phase. As a result, a decrease in surface area and changes in pore structure may occur. Thus, in order to maintain the pore structure of the wet gel, there is not only a need to substitute water having high surface tension with an organic solvent having relatively low surface tension, but also to develop a technique capable of washing and drying the wet gel without shrinkage while maintaining the structure of the wet gel as it is.

Also, the dried silica aerogel maintains low thermal conductivity immediately after the drying, but the thermal conductivity may gradually increase because a hydrophilic silanol group (Si—OH) present on the surface of silica absorbs water in the air. Thus, there is a need to modify the surface of the silica aerogel into hydrophobic to maintain low thermal conductivity. Accordingly, a method of modifying the surface of the silica aerogel by using a surface modifier has been widely used. However, since a large amount of the surface modifier is required to prepare a silica aerogel having high hydrophobicity by only using the surface modifier and it is difficult to control a surface modification reaction, productivity may be low.

Thus, the present invention provides a method of preparing a highly hydrophobic silica aerogel having excellent physical properties while maintaining a pore structure and low thermal conductivity of the silica aerogel.

Hereinafter, a method of preparing a hydrophobic silica aerogel according to an embodiment of the present invention will be described in detail with reference to FIG. 1.

FIG. 1 schematically illustrates a flowchart of the method of preparing a hydrophobic silica aerogel according to the embodiment of the present invention.

The preparation method according to the embodiment of the present invention includes the steps of: adding a water glass solution and an acid catalyst to a reactor and performing a reaction to prepare a silica wet gel (step 1); adding an inorganic acid and a surface modifier solution to the silica wet gel and performing a surface modification reaction to prepare a hydrophobic silica wet gel (step 2); and drying the hydrophobic silica wet gel (step 3), wherein the method further includes a step of adding ammonium hydroxide during the surface modification reaction of step 2.

Step 1 is a step for preparing a silica wet gel and may be performed by adding an acid catalyst to a water glass solution and performing a reaction. The reaction may be performed at a pH of 4 to 7.

Specifically, the silica wet gel may be prepared by adding the acid catalyst, after adding the water glass solution to the reactor, and performing the reaction.

Herein, the reaction may denote a sol-gel reaction, and the "sol-gel reaction" may be a reaction that forms a network structure from a silicon unit precursor material.

Herein, the network structure may denote a flat net-shaped structure, in which any specific polygons having one or more types of atomic arrangements are connected, or a structure in which a three-dimensional skeleton structure is formed by sharing vertices, edges, and faces of a specific polyhedron.

The water glass solution may denote a dilute solution in which distilled water is added to water glass and mixed, and the water glass may be sodium silicate ($Na_2SiO_3$) as an alkali silicate salt obtained by melting silicon dioxide ($SiO_2$) and alkali.

The water glass solution may contain 1 wt % to 11 wt % of silicon dioxide ($SiO_2$). In a case in which the silicon dioxide in the water glass solution is included in an amount less than the above range, an aerogel may not be formed properly, and, in a case in which the silicon dioxide in the water glass solution is included in an amount greater than the above range, a specific surface area may be reduced.

The acid catalyst may play a role in creating a reaction environment so that the reaction (sol-gel reaction) proceeds easily, and, for example, may control the reaction environment to achieve the above-described pH.

The acid catalyst is added in a molar ratio of 0.2 to 1.5 based on the water glass in the water glass solution, but may be added in an amount such that a pH value is within the above-described pH range.

The acid catalyst is not particularly limited, but may, for example, be at least one selected from the group consisting of hydrochloric acid, nitric acid, acetic acid, sulfuric acid, and hydrofluoric acid.

The preparation method according to the embodiment of the present invention may further include a step of aging the silica wet gel prepared after the reaction of step 1.

The aging is not particularly limited, but may, for example, be performed by being left standing at a temperature of 50° C. to 90° C. for 1 hour to 10 hours.

Since the aging may be performed after the preparation of the silica wet gel, the preparation method according to the embodiment of the present invention may more firmly form the network structure in the silica wet gel, and thus, pore characteristics may be excellent.

Step 2 is a step for preparing a hydrophobic silica wet gel, and may be performed by adding an inorganic acid and a surface modifier solution to the silica wet gel and performing a reaction. In this case, the inorganic acid and the surface modifier solution may be sequentially added, and, for example, after the inorganic acid is added to the silica wet gel and mixed, the surface modifier solution may be added.

Also, before the addition of the inorganic acid to the silica wet gel, a step of milling the silica wet gel may be further performed.

The inorganic acid may play a role in activating decomposition of the surface modifier by reacting with the surface modifier in the surface modifier solution to be described later, and thus, may improve the surface modification reaction. The inorganic acid is not particularly limited, but may, for example, be at least one selected from the group consisting of nitric acid, hydrochloric acid, sulfuric acid, and hydrofluoric acid. Specifically, the inorganic acid may be nitric acid.

The surface modifier solution may be prepared by adding the surface modifier to a non-polar organic solvent and mixing together, and in this case, a concentration of the surface modifier in the surface modifier solution may be in a range of 0.1 M to 4 M. That is, the surface modifier solution may be prepared by adding the surface modifier to the non-polar organic solvent in an amount of 0.1 M to 4 M and then mixing together.

Also, the surface modifier solution may be added in an amount such that a molar ratio of the surface modifier to the water glass in the water glass solution is in a range of 0.07 to 2.

In a case in which the surface modifier solution is added in an amount such that the molar ratio of the surface modifier to the water glass is less than 0.07, since the amount of the surface modifier able to react with a silanol group (Si—OH) is relatively smaller than the amount of the silanol group (Si—OH) in the water glass solution, surface modification reactivity may not only be reduced but also surface modification may not be easily performed. Accordingly, the silanol group, which is not surface-modified, causes a condensation reaction during drying so that the size of pores of the resultant silica aerogel may be decreased and porosity may not be obtained. Furthermore, in a case in which the surface modifier solution is added in an amount such that the molar ratio of the surface modifier to the water glass is greater than 2, a large amount of the remaining surface modifier, which does not participate in the surface modification reaction, may be present and economic efficiency may be reduced because the expensive surface modifier is wasted.

The surface modifier may be at least one selected from the group consisting of trimethylchlorosilane (TMCS), hexamethyldisilazane (HMDS), methyltrimethoxysilane, and trimethylethoxysilane.

The non-polar organic solvent may be at least one selected from the group consisting of hexane, heptane, toluene, and xylene.

The surface modification reaction of step 2 may be performed by adding the inorganic acid and the surface modifier solution to the silica wet gel and mixing by stirring, and the surface modification reaction may be performed at a temperature of 25° C. to 95° C.

In this case, the stirring is not particularly limited, but, for example, may be performed at a rate of 50 rpm to 700 rpm.

In the preparation method according to the embodiment of the present invention, solvent substitution may be simultaneously performed while the surface modification reaction is performed.

Specifically, in the preparation method, since the inorganic acid is added to the silica wet gel and the surface modifier solution is mixed and reacted therewith, the decomposition of the surface modifier in the surface modifier solution may be activated by the inorganic acid, and thus, the surface modification reaction may be promoted. Also, the solvent substitution may be performed while the surface modification reaction may be performed with the non-polar organic solvent included in the surface modifier solution.

In order to further promote the surface modification reaction, the preparation method may further include a step of adding ammonium hydroxide during the surface modification reaction.

Specifically, the ammonium hydroxide may be added after the entire amount of the surface modifier solution used in the surface modification reaction has been added to the reactor, and, for example, after the entire amount of the surface modifier solution has been added to the reactor, the ammonium hydroxide may be allowed to participate in the reaction by being added when the pH in the reactor reaches 5 to 10, or the ammonium hydroxide may be allowed to participate in the reaction by being added after the solvent substitution is completed.

Also, an amount of the ammonium hydroxide added is not particularly limited as long as it is an amount by which the surface modification reaction may be easily carried out without causing problems due to other addition reactions, but, for example, the ammonium hydroxide may be added in an amount such that a pH in the reactor after the addition of the ammonium hydroxide is increased by 5% to 57% in comparison to a pH in the reactor before the addition of the ammonium hydroxide. For example, in a case in which the pH in the reactor before the addition of the ammonium hydroxide is 7, the ammonium hydroxide may be added in an amount such that the pH in the reactor is in a range of 7.35 to 11.

Specifically, the ammonium hydroxide may be added in an amount such that a molar ratio of the ammonium hydroxide to the surface modifier in the surface modifier solution is in a range of 0.5 to 25 within the amount that adjusts the pH within the above range.

Since the ammonium hydroxide is allowed to participate in the reaction by being further added during the reaction of step 2, the preparation method according to the embodiment of the present invention may improve the surface modification reaction, and thus, a silica aerogel having high hydrophobicity may be prepared without using a large amount of the expensive surface modifier.

Step 3 is a step of drying the hydrophobic silica wet gel in order to prepare a hydrophobic silica aerogel.

In this case, a step of washing may be further performed before the drying.

The washing is to obtain a high purity hydrophobic silica aerogel by removing impurities (sodium ions, unreacted products, by-products, etc.) generated during the reaction, wherein the washing may be performed by a dilution process or exchange process using the non-polar organic solvent.

Specifically, the dilution process may denote a solvent dilution process and may be performed by allowing an excessive amount of the non-polar organic solvent to be present in the reactor by further adding the non-polar organic solvent to the reactor after the surface modification reaction of step 2. Also, the exchange reaction may denote a solvent exchange process, and may be performed by repeating a process, in which an aqueous solution layer in the reactor is discharged after the surface modification reaction of step 2, the non-polar organic solvent is then added, and the separated aqueous solution layer is again discharged, several times.

The drying may be performed by atmospheric pressure drying at a temperature of 100° C. to 190° C. for 1 hour to 4 hours, but the present invention is not limited thereto.

Also, the present invention provides a hydrophobic silica aerogel prepared by the above preparation method.

The hydrophobic silica aerogel according to an embodiment of the present invention may have a tap density of 0.03 g/ml to 0.15 g/ml and may contain 9 wt % to 12 wt % of carbon.

Since the hydrophobic silica aerogel according to the embodiment of the present invention is prepared by the above preparation method, the hydrophobic silica aerogel according to the embodiment of the present invention may have high hydrophobicity as well as excellent tap density characteristics.

Hereinafter, the present invention will be described in more detail, according to the following examples and experimental examples. However, the following examples and experimental examples are merely presented to exemplify the present invention, and the scope of the present invention is not limited thereto.

Example 1

3 ml of acetic acid was added to a water glass solution (containing 13.8 g of water glass) and reacted to form a silica wet gel and the silica wet gel was then aged at 50° C. for about 1 hour. Thereafter, the silica wet gel was crushed by using a milling machine and 7 g of nitric acid was then added thereto to prepare a mixed solution. A temperature in a reactor was set at 55° C. while the mixed solution was added to the reactor and stirred. Thereafter, a hexamethyldisilazane solution was added to the reactor to perform a reaction. In this case, the hexamethyldisilazane solution was prepared by adding 23 g of hexamethyldisilazane to 200 ml of n-hexane and stirring the mixture. When a pH in the reactor reached 7 after the reaction began, 2.7 g of ammonium hydroxide was added to participate in the reaction. When a prepared hydrophobic silica wet gel completely floated on a surface, 400 ml of n-hexane was added, a lower aqueous solution layer was discharged, and, after 2 hours, the hydrophobic silica wet gel was completely dried in a forced circulation dryer at 150° C. for 1 hour to prepare a hydrophobic silica aerogel.

Example 2

A hydrophobic silica aerogel was prepared in the same manner as in Example 1 except that a water glass solution including 17.2 g of water glass was used.

Example 3

A hydrophobic silica aerogel was prepared in the same manner as in Example 1 except that a water glass solution including 20.7 g of water glass was used.

Example 4

A hydrophobic silica aerogel was prepared in the same manner as in Example 1 except that 4 g of nitric acid was used and 15 g of a surface modifier was used during the preparation of the surface modifier solution.

Example 5

A hydrophobic silica aerogel was prepared in the same manner as in Example 2 except that 4 g of nitric acid was used and 15 g of a surface modifier was used during the preparation of the surface modifier solution.

Example 6

A hydrophobic silica aerogel was prepared in the same manner as in Example 3 except that 4 g of nitric acid was used and 15 g of a surface modifier was used during the preparation of the surface modifier solution.

Example 7

4 ml of acetic acid was added to a water glass solution (containing 17.2 g of water glass) and reacted to form a silica wet gel and the silica wet gel was then aged at 50° C. for about 1 hour. Thereafter, the silica wet gel was crushed by using a milling machine and 5 g of nitric acid was then added thereto to prepare a mixed solution. A temperature in a reactor was set at 55° C. while the mixed solution was added to the reactor and stirred. Thereafter, a hexamethyldisilazane solution was added to the reactor to perform a reaction. In this case, the hexamethyldisilazane solution was prepared by adding 15 g of hexamethyldisilazane to 100 ml of n-hexane and stirring the mixture. When a pH in the reactor reached 7 after the reaction began, 2.7 g of ammonium hydroxide was added to participate in the reaction. When a prepared hydrophobic silica wet gel completely floated on a surface, impurities were removed by repeating an operation, in which a lower aqueous solution layer in the reactor was discharged, 100 ml of n-hexane was again added, and a re-separated lower aqueous solution layer was then discharged, three times. After 2 hours, the hydrophobic silica wet gel was completely dried in a forced circulation dryer at 150° C. for 1 hour to prepare a hydrophobic silica aerogel.

Example 8

A hydrophobic silica aerogel was prepared in the same manner as in Example 7 except that 19 g of a surface modifier was used during the preparation of the surface modifier solution.

Example 9

A hydrophobic silica aerogel was prepared in the same manner as in Example 7 except that 23 g of a surface modifier was used during the preparation of the surface modifier solution.

Comparative Example 1

A hydrophobic silica aerogel was prepared in the same manner as in Example 1 except that the step of adding the ammonium hydroxide was omitted.

Comparative Example 2

A hydrophobic silica aerogel was prepared in the same manner as in Example 2 except that the step of adding the ammonium hydroxide was omitted.

Comparative Example 3

A hydrophobic silica aerogel was prepared in the same manner as in Example 3 except that the step of adding the ammonium hydroxide was omitted.

Comparative Example 4

A hydrophobic silica aerogel was prepared in the same manner as in Example 4 except that the step of adding the ammonium hydroxide was omitted.

Comparative Example 5

A hydrophobic silica aerogel was prepared in the same manner as in Example 5 except that the step of adding the ammonium hydroxide was omitted.

Comparative Example 6

A hydrophobic silica aerogel was prepared in the same manner as in Example 6 except that the step of adding the ammonium hydroxide was omitted.

Comparative Example 7

A hydrophobic silica aerogel was prepared in the same manner as in Example 7 except that the step of adding the ammonium hydroxide was omitted.

Comparative Example 8

A hydrophobic silica aerogel was prepared in the same manner as in Example 9 except that the step of adding the ammonium hydroxide was omitted.

Comparative Example 9

A hydrophobic silica aerogel was prepared in the same manner as in Example 7 except that 30 g of a surface modifier was used during the preparation of the surface modifier solution.

Experimental Example

In order to compare physical properties of the hydrophobic silica aerogels prepared in Examples 1 to 9 and Comparative Examples 1 to 9, tap density (g/ml) and carbon content (wt %) of each aerogel were measured. The results thereof are presented in Table 1 below.

(1) Tap Density (g/ml)

Tap density was measured using a tap density tester (STAV II, Engelsmann AG).

Specifically, after a weight of each aerogel was measured by putting the each aerogel into a standardized cylinder (25 ml), the cylinder was then fixed to the tap density tester, a noise damping hood was closed, and 2,500 tappings were set. After tapping measurement was completed, a volume of each aerogel in the cylinder was measured, and density was measured by calculating a ratio of the weight previously measured to the volume.

(2) Carbon Content (Wt %)

Carbon contents were measured using a carbon analyzer (Carbon-Sulfur Analyzer CS-2000, Eltra GmbH).

TABLE 1

| Category | Tap density (g/ml) | Carbon content (wt %) |
|---|---|---|
| Example 1 | 0.039 | 10.12 |
| Example 2 | 0.049 | 9.47 |
| Example 3 | 0.051 | 10.19 |
| Example 4 | 0.065 | 9.26 |
| Example 5 | 0.059 | 9.46 |
| Example 6 | 0.064 | 9.79 |
| Example 7 | 0.081 | 9.52 |
| Example 8 | 0.079 | 10.05 |
| Example 9 | 0.063 | 11.10 |
| Comparative Example 1 | 0.063 | 9.28 |
| Comparative Example 2 | 0.071 | 9.82 |
| Comparative Example 3 | 0.078 | 9.51 |
| Comparative Example 4 | — | — |
| Comparative Example 5 | — | — |
| Comparative Example 6 | — | — |
| Comparative Example 7 | 0.142 | 10.85 |
| Comparative Example 8 | 0.109 | 9.73 |
| Comparative Example 9 | 0.098 | 9.51 |

As illustrated in Table 1, it was confirmed that the hydrophobic silica aerogels of Examples 1 to 9 prepared by the preparation method according to the embodiment of the present invention generally had high carbon contents while having low tap densities in comparison to the hydrophobic silica aerogels of Comparative Examples 1 to 9.

Specifically, as a result of comparing the hydrophobic silica aerogels of Example 1 and Comparative Example 1, the hydrophobic silica aerogels of Example 2 and Comparative Example 2, and the hydrophobic silica aerogels of Example 3 and Comparative Example 3 which were prepared under the same conditions except whether the ammonium hydroxide was added or not, the carbon contents of the hydrophobic silica aerogels of Example 1, Example 2, and Example 3 were increased while the hydrophobic silica aerogels of Example 1, Example 2, and Example 3 had tap densities which were respectively reduced by 62%, 69%, and 65% in comparison to the hydrophobic silica aerogels of Comparative Example 1, Comparative Example 2, and Comparative Example 3.

Also, as a result of comparing the hydrophobic silica aerogels of Example 4 and Comparative Example 4, the hydrophobic silica aerogels of Example 5 and Comparative Example 5, and the hydrophobic silica aerogels of Example 6 and Comparative Example 6 which were prepared under the same conditions except whether the ammonium hydroxide was added or not, since the surface modification reaction was easily performed on the hydrophobic silica aerogels of Example 4, Example 5, and Example 6 even if a small amount of the surface modifier was used, the hydrophobic silica aerogels of Example 4, Example 5, and Example 6 had low tap densities and high carbon contents. However, since surface modification was not properly performed on Comparative Example 4, Comparative Example 5, and Comparative Example 6, good hydrophobic silica aerogels were not formed. The hydrophobic silica aerogels of Example 4, Example 5, and Example 6 respectively had equivalent levels of carbon content while respectively having lower tap densities than Comparative Example 1, Comparative Example 2, and Comparative Example 3 in which a relatively large amount of the surface modifier was used.

Also, with respect to the hydrophobic silica aerogel of Comparative Example 9 which was prepared by using a relatively large amount of the surface modifier, the tap density was increased by about 156% and the carbon content was reduced by 86% in comparison to the hydrophobic silica aerogel of Example 9 which was prepared by using a relatively small amount of the surface modifier.

The above results indicated that the surface modification reaction may be improved by adding the ammonium hydroxide in the preparation method according to the embodiment of the present invention, and thus, hydrophobicity of the hydrophobic silica aerogel prepared by the above preparation method may be improved.

The invention claimed is:

1. A method of preparing a hydrophobic silica aerogel, the method comprising steps of:
   (1) adding a water glass solution and an acid catalyst to a reactor and performing a reaction to prepare a silica wet gel;
   (2) adding an inorganic acid and a surface modifier solution to the silica wet gel and performing a surface modification reaction comprising adding ammonium hydroxide after an entire amount of the surface modifier solution is added to prepare a hydrophobic silica wet gel; and
   (3) drying the hydrophobic silica wet.

2. The method of claim 1, wherein the water glass solution contains 1 wt % to 11 wt % of silicon dioxide ($SiO_2$).

3. The method of claim 1, wherein the acid catalyst is used present in a molar ratio of 0.2 to 1.5 based on water glass in the water glass solution.

4. The method of claim 1, wherein aging is performed after the reaction of step 1, and
   wherein the aging is performed by maintaining at a temperature of 50° C. to 90° C. for 1 hour to 10 hours.

5. The method of claim 1, wherein the silica wet gel is milled before adding the inorganic acid in step 2.

6. The method of claim 1, wherein the surface modifier solution is prepared by adding a surface modifier to a non-polar organic solvent and mixing together, and
   a concentration of the surface modifier in the surface modifier solution is in a range of 0.1 M to 4 M.

7. The method of claim 6, wherein the surface modifier comprises at least one selected from the group consisting of trimethylchlorosilane (TMCS), hexamethyldisilazane (HMDS), methyltrimethoxysilane, and trimethylethoxysilane, and
   wherein the non-polar organic solvent comprises at least one selected from the group consisting of hexane, heptane, toluene, and xylene.

8. The method of claim 1, wherein the surface modifier solution is added in an amount such that a molar ratio of a surface modifier to water glass in the water glass solution is in a range of 0.07 to 2.

9. The method of claim 1, wherein the surface modifier solution is added when the inorganic acid is added to the silica wet gel and a temperature in the reactor reaches 25° C. to 95° C.

10. The method of claim 1, wherein, after an entire amount of the surface modifier solution is added, the ammonium hydroxide is added when a pH in the reactor reaches 5 to 10.

11. The method of claim 1, wherein the ammonium hydroxide is added in an amount such that a pH in the reactor after the addition of the ammonium hydroxide is increased by 5% to 57% in comparison to a pH in the reactor before the addition of the ammonium hydroxide.

12. The method of claim 1, wherein the ammonium hydroxide is added in an amount such that a molar ratio of the ammonium hydroxide to a surface modifier in the surface modifier solution is in a range of 0.5 to 25.

13. The method of claim 1, further comprising washing the hydrophobic silica wet gel before the drying of step (3), and
   wherein the washing is performed by a dilution process or an exchange process using a non-polar solvent.

* * * * *

UNITED STATES PATENT AND TRADEMARK OFFICE
CERTIFICATE OF CORRECTION

PATENT NO.        : 10,294,111 B2
APPLICATION NO.   : 15/527663
DATED             : May 21, 2019
INVENTOR(S)       : Young Hun Kim et al.

Page 1 of 1

It is certified that error appears in the above-identified patent and that said Letters Patent is hereby corrected as shown below:

In the Claims

At Column 11, Line 39 to Line 51, please replace Claim 1 with the following:
1. A method of preparing a hydrophobic silica aerogel, the method comprising steps of:
 (1) adding a water glass solution and an acid catalyst to a reactor and performing a reaction to prepare a silica wet gel;
 (2) adding an inorganic acid and a surface modifier solution to the silica wet gel and performing a surface modification reaction comprising adding ammonium hydroxide after an entire amount of the surface modifier solution is added to prepare a hydrophobic silica wet gel; and
 (3) drying the hydrophobic silica wet gel.

At Column 12, Line 3 to Line 5, please replace Claim 3, with the following:
3. The method of claim 1, wherein the acid catalyst is present in a molar ratio of 0.2 to 1.5 based on water glass in the water glass solution.

Signed and Sealed this
Sixth Day of August, 2019

Andrei Iancu
*Director of the United States Patent and Trademark Office*